United States Patent [19]
Spani et al.

[11] Patent Number: 5,440,936
[45] Date of Patent: Aug. 15, 1995

[54] COMPACT X-CROSS TRANSDUCER ARRAY FOR A TRANSIT TIME FLOWMETER, PARTICULARLY FOR USE DURING IN-VIVO BLOOD FLOW MEASUREMENT

[75] Inventors: Wayne M. Spani; William S. Kemper, both of San Diego, Calif.

[73] Assignee: Triton Technology, Inc., San Diego, Calif.

[21] Appl. No.: 977,143

[22] Filed: Nov. 16, 1992

[51] Int. Cl.⁶ ............................................. G01F 1/00
[52] U.S. Cl. .................... 73/861.28; 73/861.27; 128/661.09
[58] Field of Search ........... 73/861.27, 861.28, 861.29, 73/861.31

[56] References Cited

U.S. PATENT DOCUMENTS

| | | | |
|---|---|---|---|
| 2,826,912 | 3/1958 | Kritz | 73/861.27 |
| 2,993,373 | 7/1961 | Kritz | 73/861.29 |
| 3,282,101 | 11/1966 | Yamamoto | 73/861.27 |
| 3,555,899 | 1/1971 | Yamamoto et al. | 73/861.27 |
| 3,564,912 | 2/1971 | Malone et al. | 73/861.31 |
| 3,625,057 | 12/1971 | Yoshiyama et al. | 73/861.27 |
| 3,940,985 | 3/1976 | Wyler | 73/861.31 |
| 4,024,760 | 5/1977 | Estrada, Jr. | 73/861.31 |
| 4,028,938 | 6/1977 | Eck | 73/861.31 |
| 4,109,523 | 8/1978 | Teyssandier | 73/861.31 |
| 4,408,589 | 10/1983 | Hauler et al. | 73/861.27 |
| 4,557,148 | 12/1985 | Akiyama | 73/861.28 |
| 4,646,575 | 3/1987 | O'Hair et al. | 73/861.31 |
| 5,040,415 | 8/1991 | Barkoudarian | 73/861.27 |

Primary Examiner—Richard E. Chilcot, Jr.
Assistant Examiner—R. L. Biegel
Attorney, Agent, or Firm—William C. Fuess

[57] ABSTRACT

Multiple, typically four, acoustic transducers of a time delay acoustic flowmeter are arrayed in a X-cross, criss-cross, folded geometry so as to establish a lengthy multiple-leg, typically a two-leg, acoustic path within a compact volume. An ultrasonic signal is transmitted from a transducer A to a transducer B, then electrically amplified and applied to a transducer C which retransmits the ultrasonic signal to a transducer D. The compact transducer configuration is particularly suitable for use during in-vivo blood flow measurement. The acoustic signal is maintained in amplitude from one leg to the next by amplification as an electrical signal.

9 Claims, 6 Drawing Sheets

PRIOR ART

FIG. 1

PRIOR ART

FIG. 2

PRIOR ART

FIG. 3

PRIOR ART

COMPACT X-CROSS TRANSDUCER ARRAY FOR A TRANSIT TIME FLOWMETER, PARTICULARLY FOR USE DURING IN-VIVO BLOOD FLOW MEASUREMENT

REFERENCE TO RELATED APPLICATIONS

The present patent application is related to U.S. Pat. No. 5,363,848, issued Nov. 15, 1994 and entitled VARIABLE ACOUSTIC ILLUMINATION OF A LUMEN FLOWING FLUID IN ORDER COMPENSATE FOR DIFFERING ACOUSTIC ATTENUATIONS, PARTICULARLY DURING ACOUSTIC BLOOD FLOW MEASUREMENT The related application is to the same inventors as is the present application.

BACKGROUND OF THE INVENTION

1. Field of the Invention

The present invention generally concerns the acoustic measurement of fluid flow velocity within a lumen; particularly the in-vivo measurement of blood flow in a blood vessel by a transit time acoustic flowmeter.

The present invention particularly concerns a spatial, and an electrical, configuration of multiple transducers within a transit time acoustic flowmeter in order that the size of an acoustic probe may be minimized in both length and diameter-while the acoustic path over which acoustic propagation delay is measured is maximized.

2. Description of the Prior Art

2.1 General Operation of Acoustic Flowmeters and Associated Sonic Transducers The transit time of sound projected diagonally across a flowing fluid has been used to measure the rate of the fluid's flow. The flowing fluid is normally contained in a conduit, or lumen. In various forms of transit time and Doppler type acoustic flowmeters one or more sonic transducers are used. In one common form of a transit time acoustic flowmeter two transducers are positioned against a lumen flowing fluid and diagonally across the lumen from each other. One transducer is located in a relatively more upstream, and the other in a relatively more downstream, position. Sound is transmitted through the flowing fluid between the transducers in each of the Upstream and downstream directions.

The bi-directional acoustic signals are variably delayed by their passage through the flowing fluid. Measurement of difference between the acoustic signal delay, or phase shift, in the upstream and downstream sound propagation directions is indicative of the velocity of fluid flow in the lumen between the transducers. Previous transit time acoustic flowmeters have used various acoustic modulation and demodulation schemes in combination with continuous, or pulsed, ultrasound.

In previous transit time flowmeters acoustic signals have either been alternately or simultaneously transmitted along opposing paths between one or more pairs of transducers. Most commonly transit time flowmeters send acoustic signals alternately in the upstream (obliquely across a lumen flowing fluid) and downstream directions. More rarely, some transit time flowmeters send an acoustic signal upstream between the transducers of one transducer pair simultaneously that another acoustic signal is sent downstream between the transducers of another transducer pair. The previous transit time flowmeter employing multiple transducer pairs, and multiple acoustic paths between the transducers, is most closely analogous to the present invention.

However, the present invention will be seen to function differently from previous transit time flowmeters using multiple pairs of transducers in that an acoustic signal will be sent between the transducers of two successive transducer pairs in the same—as opposed to opposite—upstream/downstream direction. The propagation on the two successive acoustic paths will be seen to be successive in that propagation will not start upon a second acoustic path until it has previously commenced upon a first. acoustic path. However, the propagation on the two successive acoustic paths will also be seen to be simultaneous in that an acoustic signal will typically sequentially commence propagation upon the second acoustic path so quickly that a first acoustic signal will still, simultaneously, be in progress upon a first acoustic path. As is typical, and even fundamental, to transit time flowmeters, the acoustic signals on both acoustic paths of the present invention will be seen to, at a later time, pass between the same pairs of transducers in the reverse direction. This later passage of acoustic signals will again be—collectively as between the transducers of all transducer pairs—in the same upstream/downstream direction. Accordingly, and notably, in the present invention an acoustic signal between the two transducers of each of a number (typically two) of transducer pairs will be seen to propagate both (i) sequentially and (ii) simultaneously in a same—as opposed to an opposite—direction relative to the upstream-downstream direction of the flowing fluid.

2.2 Full Acoustic Illumination of the Flowing Fluid by the Transducers

Some previous acoustic flowmeters used small transducers which only served to acoustically illuminate only a central portion of fluid flowing within a lumen. The velocity of the flowing fluid was measured at, and for, only the acoustically illuminated (central) portion of the lumen. Fluid flow within a lumen is typically laminar, and non-turbulent, with a stratified profile of flow velocity. In such a stratified profile of flow velocity the fluid flows fastest at the center of the lumen and slowest along the lumen's wall(s). Accordingly, a measurement of the velocity of fluid flow only at the central portion of the lumen, howsoever accurate, cannot, by definition, be truly indicate of the average velocity of fluid flow throughout the entire cross-sectional area of the lumen.

Improvements have been made to acoustic flowmeters in order to more correctly measure the flow of fluid within a lumen when the fluid is flowing at a complex profile of flow velocity. Reference U.S. Pat. Nos. 3,575,050 for a "Fluid Flowmeter" and 3,906,791 for an "Area Averaging Ultrasonic Flowmeter" to Lynnworth. One improvement was to use wide transducers, normally so wide so as to evenly acoustically illuminate the entire cross section of fluid flowing within a lumen. By this method the velocity of fluid flow could be area averaged over all, or substantially all, of the lumen's cross-sectional area, and a the average fluid flow velocity within the lumen could be more accurately determined. The present invention will be seen to function for full acoustic illumination of the fluid flowing within the lumen—as is desirable—while functioning to do so in a particularly compact geometry.

2.3 Sensitivity of Acoustic Flow Measurement to Alignment of the Transducers With the Flow Axis Acoustic fluid flow measurement systems developed and shown by Lynnworth in U.S. Pat. No. 3,906,791, by Drost in U.S. Pat. No. 4,227,407, and by others place both transducers on the same side of a conduit and use a sound reflecting surface, or reflecting-type transducer, to reflect the sound beam off the far wall of the conduit. This configuration is widely used for the measurement of fluid flow through closed channels in industrial applications. It has been shown that the reflecting technique makes a first order correction for alignment errors under conditions where the flow axis of the conduit is not aligned with the transducer array axis and the flow conduit is substantially smaller than the transducer array. The sound reflector is rather long and oddly shaped which, combined with its weight, makes it disadvantageous for implantation within a living animal for blood flow measurement applications, especially those persisting over a long term.

The present invention will be seen to enjoy the same insensitivity to alignment between the transducers and the flow axis as is realized in the prior art without the necessity, and attendant size and weight penalty, of using a sound reflector.

SUMMARY OF THE INVENTION

The present invention contemplates acoustic transducers arrayed in a folded geometry. Two pairs of acoustically-coupled transducer of a transit-time acoustic flowmeter are (i) electrically connected, and (ii) spatially aligned in a particular crisscross, X-cross, folded geometry. The (i) electrical connection and (ii) X-cross geometry serves to establish a long acoustic path in a compact volume. The compact transducer configuration is particularly suitable for use during in-vivo blood flow measurement where it is typically difficult to expose a long segment of a blood vessel to the transducer array, and wherein the size and volume of implanted acoustic transducers may adversely affect the animal.

The present invention further contemplates the transmission and reception of acoustic signals along each of successive legs of a multi-leg acoustic path. An acoustic signal containing flow information from its passage through the flowing fluid of a lumen along one acoustic path, or leg, is (i) transduced in a receiving transducer to an electrical signal, (ii) electrically communicated to a next, transmitting, transducer on a next leg, (iii) transduced in this transmitting transducer to sound, and (iv) acoustically transmitted upon the next leg. The signal is preferably enhanced by amplification between each successive leg of the multi-leg acoustic path. The legs of the multi-leg acoustic path are normally spatially arranged so as to be crisscrossing in a compact area.

In one preferred embodiment of a transducer array in accordance with the present invention, (i) two pairs of acoustic transducers are (ii) electrically connected by one amplifier with (ii) each acoustic transducer pair defining an acoustic path that intersects the acoustic path of the other transducer pair.

In the preferred embodiment of an acoustic transit-time flowmeter in accordance with the present invention, the four acoustic transducers are arranged, and acoustically and electrically interconnected, in a particular geometry. A first, acoustically transmitting, transducer is located alongside a conduit flowing a fluid so as to acoustically project a first acoustic signal (i) obliquely across the flowing fluid (ii) in a first upstream/downstream direction relative to the fluid flow (iii) along a first acoustic path. A first acoustically receiving transducer is located alongside the same conduit flowing fluid in a position diagonally opposite from the first transmitting transducer so as to receive (i) the first acoustic signal from the first transmitting transducer (ii) obliquely across the flowing fluid (iii) along the first acoustic path.

A second acoustically transmitting transducer is also located alongside the conduit flowing fluid, but at a position displaced from the first receiving transducer in a direction opposite to the first flow direction. It projects a second acoustic signal (i) obliquely across the flowing fluid (ii) again in the first direction (iii) along a second acoustic path. A second receiving transducer is located alongside the conduit flowing fluid diagonally oppositely from the second transmitting transducer so as to receive (i) the second acoustic signal from the second transmitting transducer (ii) obliquely across the flowing fluid (iii) along the second acoustic path.

Finally, the first receiving transducer is electrically connected to the second transmitting transducer. In this arrangement the first acoustic path and the second acoustic path are in the same direction relative to fluid flow within the conduit.

The first acoustically transmitting transducer is preferably positioned diagonally across the conduit flowing fluid from the first acoustically receiving transducer, thereby forming a first leg "/" of the letter "X". The second transmitting transducer is positioned diagonally across the conduit flowing fluid from the second receiving transducer, thereby forming a second leg " \ " of the letter "X". By this spatial orientation the first acoustic path and the second acoustic path are folded, with one path overlapping the other. Acoustic propagation upon the two paths is in the same directional sense at the same time; thus the flow components of the acoustic signals on both paths are additive. Also, a region of the volume of located at the intersection of the diagonal first and second legs of the letter "X" is acoustically illuminated by both the first and the second acoustic transmitter.

Still further in the preferred embodiment of the acoustic transit-time flowmeter in accordance with the present invention, the electrical connection is made by, and through, an amplifier. The amplifier serves to amplify an electrical signal produced by the first acoustically receiving transducer (in response to its receipt of an acoustic wave) and communicate this amplified electrical signal to the second transmitting transducer where it is transduced into an acoustic wave.

These and other aspects and attributes of the present invention will become increasingly clear upon reference to the following drawings and accompanying specification.

DESCRIPTION OF THE PREFERRED EMBODIMENT

The present invention overcomes many of the complications of transducer placement in previous acoustic fluid flow measurement systems. In the most common previous embodiment of a transit time acoustic flowmeter, shown in FIG. 1, two transducers 10, 11 were located obliquely across a lumen 12 flowing fluid from each other. In this embodiment both upstream and downstream transit-time measurements are made alternately. The flowmeter uses a master oscillator (not shown) for a time base and memory elements (not shown) to store transit-time information. A transmitter source of electrical energization TRANS 13 is gated in switches 14 by the flowmeter timing circuitry 15 to first energize one of the transducers 10, 11 to emit an acoustic signal, after which time the other transducer caused to emit an acoustic signal. The acoustic signal is received in the other, non-transmitting one, of the transducers 10, 11 and converted to an electrical signal. The electrical signal is gated by switches 14 to a respective receiver 16, 17. The received acoustic signals amplified by the receivers 16, 17 are fed into a circuit 18 which measures the phase difference between the received signal and the master oscillator signal. This phase difference is indicative of the time of transit, and thus of the rate of fluid flow. The averaged phase shift of the received signals across the transducers is then used to update one of two memory elements (not shown, within the circuit 18).

Figure 1:
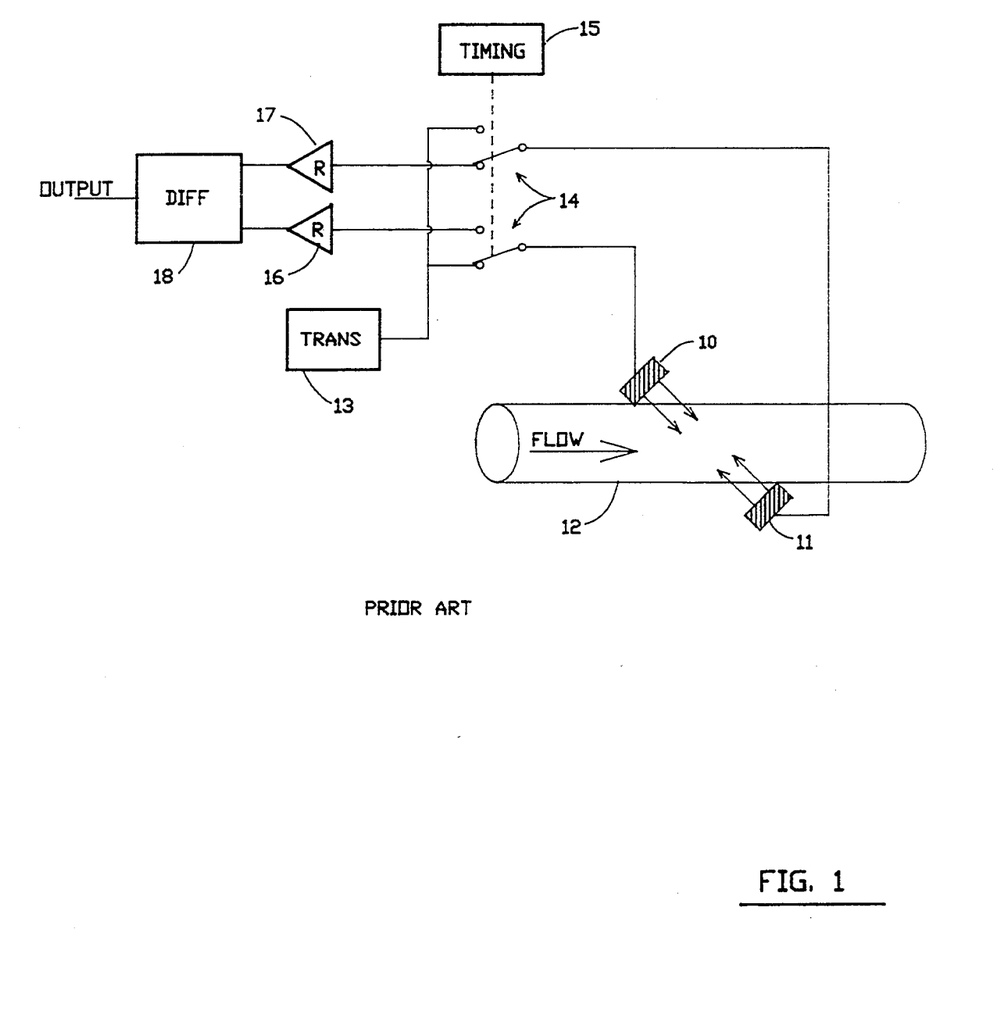
FIG. 1 is a diagram of a prior art transit time flowmeter showing the locations of, and bi-directional acoustic signals between, two acoustic transducers.

After waiting to let all acoustic echoes die out, the roles of transmitting and receiving transducer are reversed for a measurement of transit-time in the opposite upstream/downstream direction. The resulting phase shift is again stored, now in the other memory element (not shown). The difference between the two stored values is representative of the difference in acoustic propagation upstream and downstream in the flowing fluid, and thus of the rate of fluid flow. This sequence of measurements is typically repeated at intervals shorter than the fluid can appreciably change velocity, typically every few milliseconds.

Figure 2:
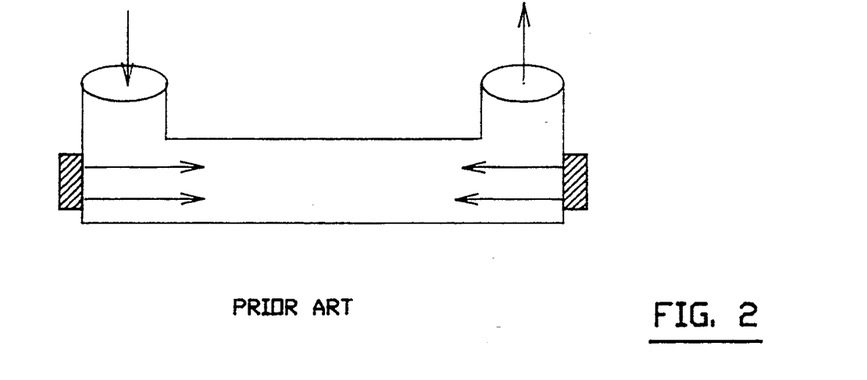
FIG. 2 is a diagram of one prior art spatial arrangement of two acoustic transducers of a transit time acoustic flowmeter.
Figure 3:
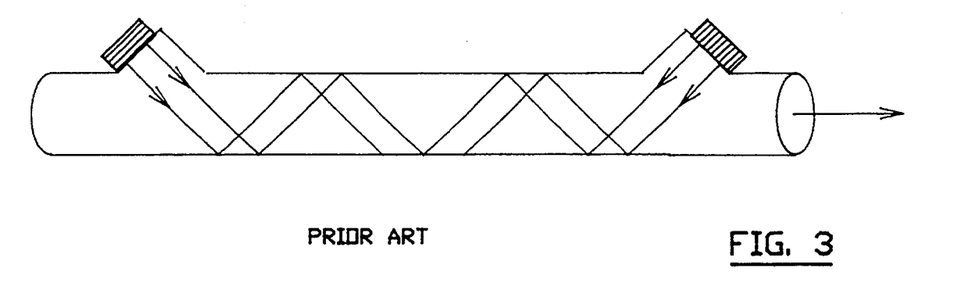
FIG. 3 is a diagram of another prior art spatial arrangement of two acoustic transducers of a transit time acoustic flowmeter.

The transducers of a transit time flowmeter can be arranged in several configurations relative to the lumen flowing fluid, and relative to the fluid flow within the lumen. Two such prior art configurations are illustrated in FIGS. 2 and 3.

Figure 4:
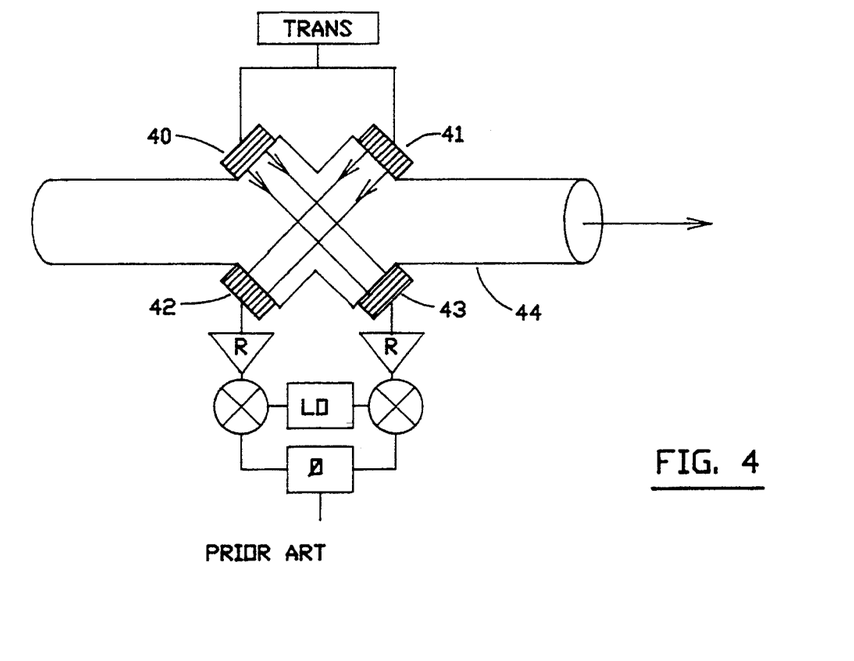
FIG. 4 is a diagram of a prior art spatial arrangement of two pairs, or four, acoustic transducers of a transit time acoustic flowmeter, the diagram showing the direction of the acoustic signals between the two acoustic transducers of each transducer pair.

One less common prior transducer configuration is illustrated in FIG. 4. Two transducer pairs, or four total transducers 40–43 are used. The transducers 40–43 may even be spaced and oriented along the lumen 44 so as to define intersecting acoustic paths, as illustrated. However, acoustic communication between the transducers of each transducer pair 40, 43 and 41, 42 is strictly unidirectional. The advantage of continuous simultaneous upstream/downstream measurements as shown in FIG. 4 is that any need for storage in order to develop the flow signal is eliminated. The present invention will immediately next be seen to (i) daisy chain, meaning electrically connect, transducer pairs, and to (ii) cause the (interconnected) pairs to transmit an acoustic signal, at any one time, in the same upstream or downstream direction—unlike the prior art configuration shown in FIG. 4.

Figure 5:
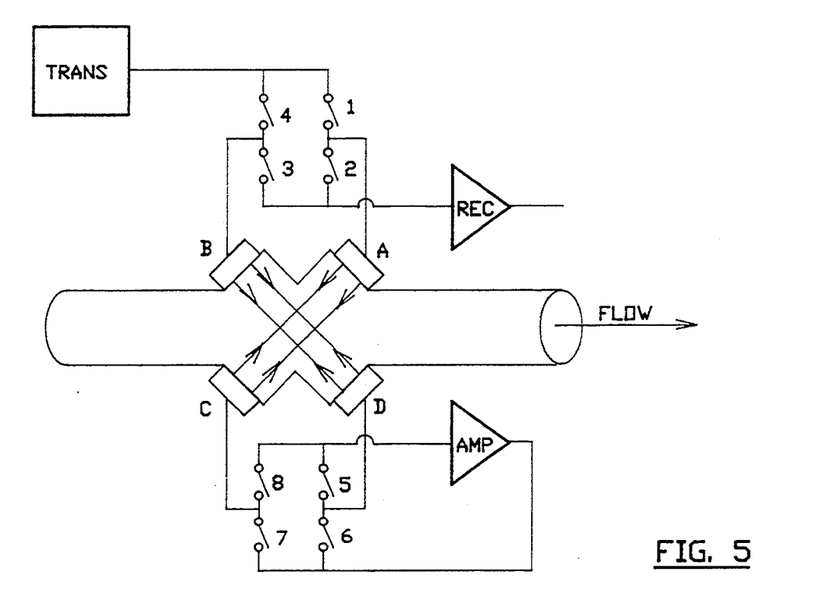
FIG. 5 is a diagram of the X-cross spatial arrangement of two pairs of acoustic transducers, or four individual acoustic transducers, of a first, preferred, embodiment of a transit time acoustic flowmeter in accordance with the present invention wherein the signal is amplified between acoustic paths, the diagram depicting the bi-directional acoustic signals between the two acoustic transducers of each of the two transducer pairs.

The preferred embodiment of the present invention wherein two pairs of acoustic transducers in a X-cross configuration define intersecting acoustic paths is shown in FIG. 5. Strip transducers 50–53 illuminate the entire cross section of flowing fluid within lumen 54 from side to side. In accordance with existing principles for a transit time flowmeter, a flow velocity profile so illuminated is area averaged, and an average flow rate for the acoustically illuminated region is derived.

Notably, the X-cross transducer arrangement in accordance with the present invention results in a flow probe which is approximately on-half as long as previously-used reflecting transducer arrangements.

Figure 6:
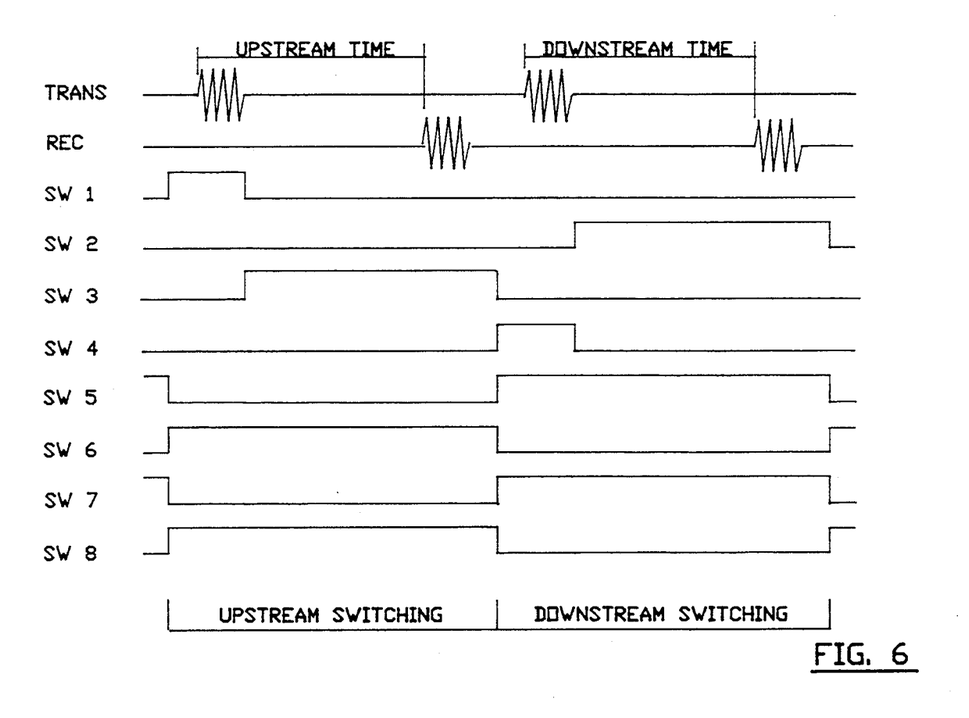
FIG. 6 is a timing diagram showing the sequence of the opening and closing of the switches 1–8 shown in FIG. 5, and the resulting transmitted and received acoustic signals.

The typical sizes of the transducers range from 10–30 mm. Typically a family of typically 11 four-transducer probes of various sizes will be spread over this size range. A preferred packaging of a four-transducer probe in accordance with the present invention is shown in FIG. 6. Each of the four transducers is held in contact with a lumen that passes through the central bore of the transducer housing. The transducers are maintained in proper alignment to each other, and at a oblique angle of nominally 45° with the axis of the lumen, and the flow of fluid therein. The exterior of the housing is normally spheroidal, and without sharp edges. Necessary electrical connections to the transducers are via percutaneous wires. The entire assembly is compact, and well suited for implantation during in-vivo blood flow measurements.

Further in accordance with the present invention, the transit time between the transducers of the variously-sized arrays is used to automatically (i) discriminate the particular probe size in use and, because the geometric size of this probe, once identified, is known with precision, to (ii) set the system amplification to achieve the properly calibrated voltage outputs.

A timing diagram of the sequence of the opening and closing of the switches 1–8 shown in FIG. 5, and the resulting transmitted and received acoustic signals, is shown in FIG. 6.

Another, second, embodiment of a transit time acoustic flowmeter in accordance with the present invention is shown in FIG. 6, In this embodiment the acoustic signal is not amplified between its propagation upon the first and second acoustic path. The X-cross spatial arrangement of two pairs of acoustic transducers, or four individual acoustic transducers, and the sequence of the bi-directional propagation of the acoustic signals between the two acoustic transducers of each of the two transducer pairs, remains the same as in the previous embodiment shown in FIG. 5.

The simplified embodiment of FIG. 6, which dispenses with electronic amplification of the transduced acoustic signal between paths, may be used where (i) the first acoustic signal initially propagated by the first transmitting transducer is sufficiently strong relative to the distance, and the attenuation, of the acoustic path over which it travels, (ii) the first receiving transducer sufficiently sensitive and efficient to convert acoustic energy into electrical energy, (iii) the resistance losses on the electrical path low, (iv) the second transmitting transducer is efficient to convert the electrical signal with which it is supplied into the second acoustic signal, and (v) the second receiving transducer is sensitive, and efficient. Because all these factors are difficult to account for with variously-sized acoustic probes (i.e., X-cross arrays of transducers) used in various environments and applications, the amplification of the first embodiment (shown in FIG. 5) is preferred. The simplified embodiment of FIG. 7 does, however, present fewer switches, a timing diagram of the sequence of the opening and closing of which, and the resulting transmitted and received acoustic signals, is shown in FIG. 8.

Figure 9:
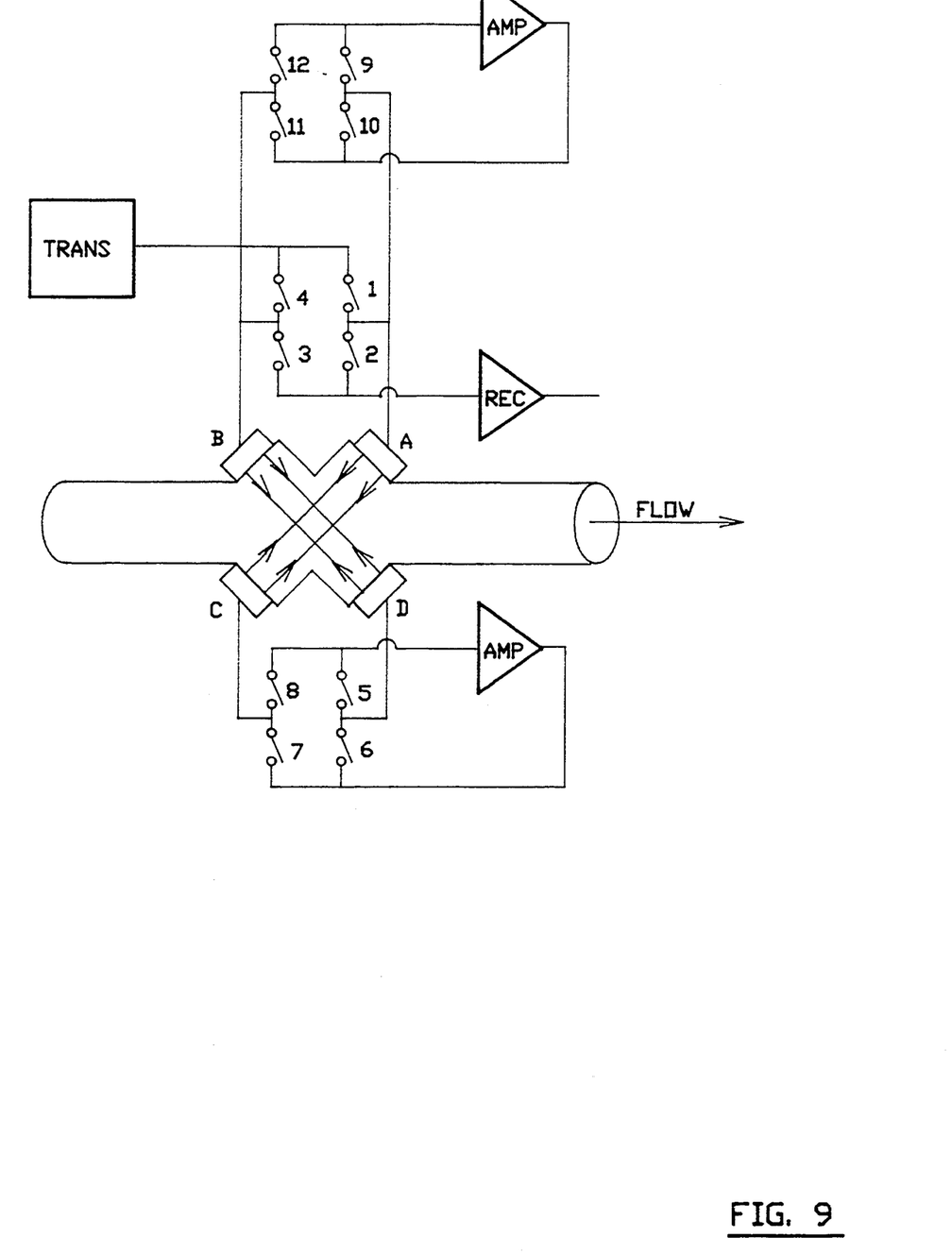
FIG. 9 is a diagram of the X-cross spatial arrangement of two pairs of acoustic transducers, or four individual acoustic transducers, of a third embodiment of a transit time acoustic flowmeter in accordance with the present invention wherein acoustic signal propagation may be repetitive in a looped path, the diagram depicting the bi-directional acoustic signals between the two acoustic transducers of each of the two transducer pairs.

A diagram of the X-cross spatial arrangement of two pairs of acoustic transducers, or four individual acoustic transducers, of a third embodiment of a transit time acoustic flowmeter in accordance with the present invention is shown in FIG. 9. In this embodiment acoustic signal propagation is repetitive for an arbitrary number of cycles in a looped path. As before, the acoustic signals are bi-directional at separate times between the two acoustic transducers of each of the two transducer pairs.

The third embodiment of FIG. 9 permits multiple passes of the acoustic signal in each direction. This operation has the advantage of increasing the cumulative phase delay by the number of passes. In operation an initial sound burst is transmitted and immediately thereafter the recirculating amplifiers are connected. The signal is allowed to circulated for N passes, such as by use of a counter and switch control logic dependent upon the cycle count (not shown). At the completion of N cycles, the acoustic signal is gated off through the final receiver for further processing in accordance with the principles of a transit time flowmeter.

An equivalent sequence is then initiated for acoustic signal propagation in the reverse direction. The multi-path multi-leg cumulative acoustic signal resultant therefrom may be processed, and compared with the multi-path acoustic signal from the opposite propagation, equivalently as in the comparison of signals is a single-pass embodiment of the flowmeter. The amplifiers AMP desirably employ Automatic Gain Control (AGC) in order to maintain the electric, and acoustic, signal level constant throughout all the propagation cycles.

The sequence of the actuation of switches 1–12 as are shown in FIG. 9 is as follows. For the initial transmission, switches 1–12 are respectively ON, OFF, OFF, OFF, OFF, ON, OFF, ON, OFF, OFF, OFF and OFF. For each of N cycles of acoustic signal recirculation the switches 1–12 are respectively set OFF, OFF, OFF, OFF, OFF, ON, OFF, ON, OFF, ON, OFF, and ON. Finally, for receipt and processing of the acoustic signal transmitted in the first, upstream, direction, the switches 1–12 are respectively set OFF, OFF, ON, OFF, OFF, OFF, OFF, OFF, OFF, OFF, OFF and OFF.

For the acoustic signal transmission in the opposite, downstream, direction switches 1–12 are respectively initially set OFF, OFF, OFF, ON, ON, OFF, ON, OFF, OFF, OFF, OFF and OFF. For each of N cycles of acoustic signal recirculation the switches 1–12 are respectively set OFF, OFF, OFF, OFF, ON, OFF, ON, OFF, ON, OFF, ON, and OFF. Finally, for receipt and processing of the acoustic signal transmitted in the second, downstream, direction, the switches 1–12 are respectively set OFF, ON, OFF, OFF, OFF, OFF, OFF, OFF, OFF, OFF and OFF.

Figure 7:
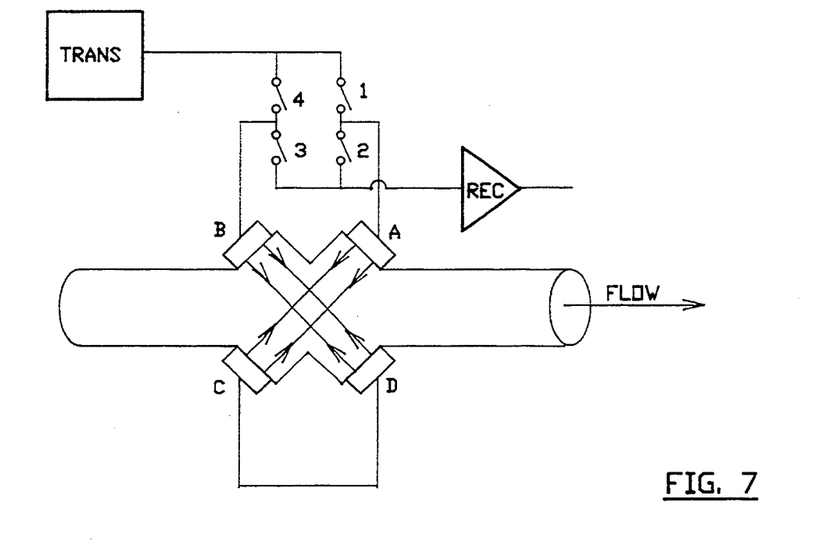
FIG. 7 is a diagram of the X-cross spatial arrangement of two pairs of acoustic transducers, or four individual acoustic transducers, of a second embodiment of a transit time acoustic flowmeter in accordance with the present invention wherein the acoustic signal is not amplified between propagation upon a first and a second acoustic path, the diagram depicting the bi-directional acoustic signals between the two acoustic transducers of each of the two transducer pairs.
Figure 8:
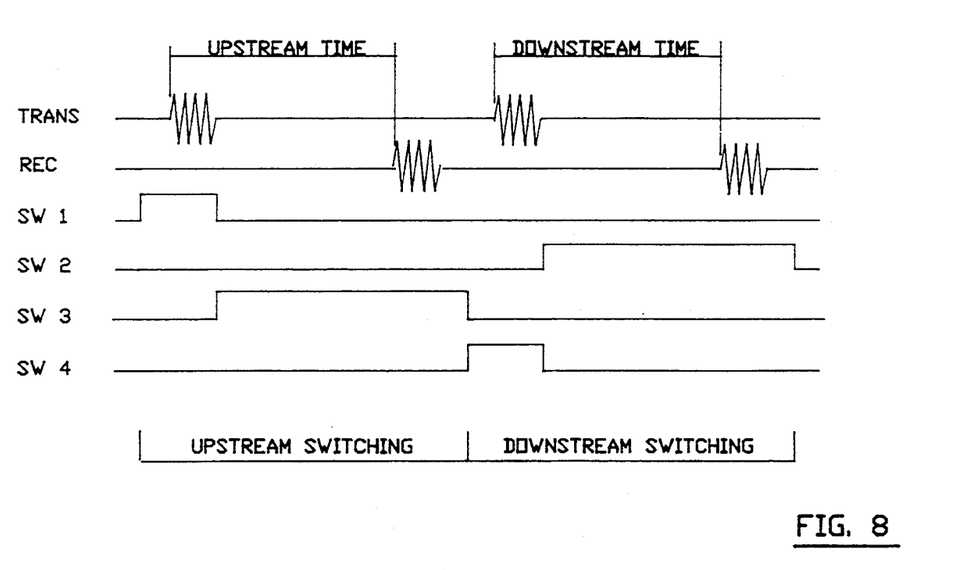
FIG. 8 is a timing diagram showing the sequence of the opening and closing of the switches 1–4 shown in FIG. 7, and the resulting transmitted and received acoustic signals.
Figure 10A:
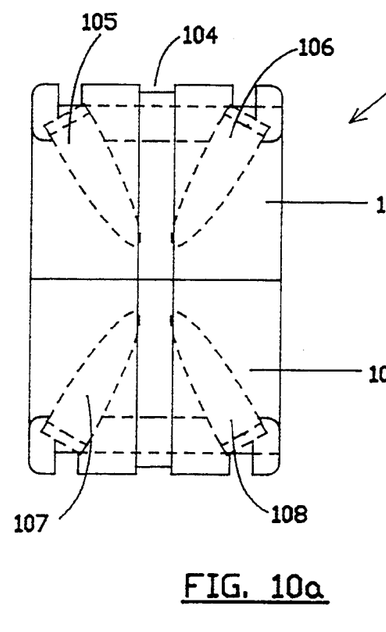
FIG. 10 is a mechanical schematic drawing of a preferred embodiment housing for the two pairs of, or four, acoustic transducers in the X-cross spatial arrangement, previously seen in FIGS. 5, 7 and 9, in accordance with the present invention.
Figure 10B:
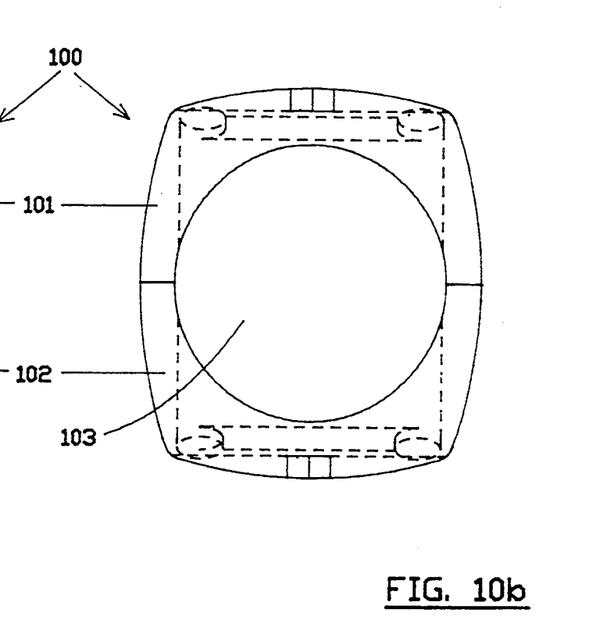

FIG. 10, consisting of FIG. 10a and FIG. 10b, is a mechanical schematic drawing of a preferred embodiment housing for the two pairs of, or four, acoustic transducers in the X-cross spatial arrangement, previously seen in FIGS. 5, 7 and 9, in accordance with the present invention. The generally spheroidally shaped housing 100, typically made of biologically inert thermoplastic, is assembled from two hemispherical sections 101, 102. The sections 101, 102 snap together to define a central channel, or bore, 103. The size of the housing 1000 is selected so that a blood vessel (not shown), fits snugly within its bore. After assembly, a stainless steel clip, nylon band, or the like fitting may be snapped or tied around circumferential groove 84 in order to maintain the two sections 81, 82 in secure contact, and tight against the contained lumen or blood vessel.

Continuing in FIG. 10, the four transducers A, B, C and D (shown in FIGS. 5, 7, and 9) are held in an X-cross pattern by being fitted within cavities 105–108. The cavities cause the contained and held transducers (not shown in FIG. 10, shown in FIGS. 5, 7 and 9) to be aligned diagonally opposite to each other across the contained lumen or blood vessel (not shown), and at a 45° angle to the axis of fluid flow within the lumen. Electrical connection to the packaged and housed transducers is made by a conventional, biologically inert, cable (not shown).

In accordance with the preceding explanation, the present invention should be interpreted broadly, and in accordance with the following claims only, and not solely in accordance with that particular embodiment within which the invention has been taught.

What is claimed is:

1. An acoustic transit-time flowmeter comprising:
    a first acoustic transmitter means, located at and acoustically coupled to a first side of a conduit flowing a fluid, for projecting a first acoustic signal (i) in a first acoustic path (ii) proceeding diagonally across the conduit and across the fluid flowing in the conduit, the diagonal first acoustic path having a vector component relative to the fluid flow that is (iii) in a first direction relative to the fluid flow;

a first acoustic receiver means, acoustically coupled to a second side, opposite to the first side, of the conduit flowing fluid in a position that is displaced in the first direction, and that is diagonally opposite, from the first acoustic transmitter means, for receiving the first acoustic signal (i) in the first acoustic path (ii) from diagonally across the conduit and across the fluid flowing in the conduit (iii) from the first acoustic transmitter means, and for transducing the received first acoustic signal into a first electrical signal;

a second acoustic transmitter means, receiving the first electrical signal from the first acoustic receiver means located at and acoustically coupled to the conduit flowing fluid on the first side thereof at a position that is displaced from the first acoustic receiver in a second direction, opposite to the first direction, for, responsive to the electrical signal, projecting a second acoustic signal (i) in a second acoustic path (ii) diagonally across the conduit and across the fluid flowing in the conduit, the diagonal second acoustic path having a vector component relative to the fluid flow that is (iii) in the first direction relative to the fluid flow;

a second acoustic receiver means, located and acoustically coupled to the second side of the conduit flowing fluid in a position that is diagonally opposite from the second acoustic transmitter means and displaced from the first acoustic transmitter in the first direction, for receiving the second acoustic signal (i) from the second acoustic path (ii) from diagonally across the conduit and across the fluid flowing in the conduit from the second acoustic transmitter means, and for transducing the received second acoustic signal into a second electrical signal.

2. The acoustic transit-time flowmeter according to claim 1
wherein the first acoustic path and the second acoustic path are symmetric about an imaginary central axis to the conduit.

3. The acoustic transit-time flowmeter according to claim 1 further comprising in a path of the first electrical signal between the first acoustic receiver means and the second acoustic transmitter means:
an amplifier for amplifying the first electrical signal produced by the first acoustic receiver means during its electrical communication to the second acoustic transmitter means.

4. The acoustic transit-time flowmeter according to claim 1 wherein the first acoustic receiver means comprises:
a first-acoustic-path first transducer for receiving the first acoustic signal during a first time and, further, for projecting at a second time separate from the first time a third acoustic signal (i) diagonally across the flowing fluid (ii) along the first acoustic path (iii) in the second direction;

and wherein the first acoustic transmitter means comprises:
a first-acoustic-path second transducer for projecting the first acoustic signal during the first time and, further, for acoustically receiving at the second time the third acoustic signal (i) diagonally across the flowing fluid (ii) along the first acoustic path (iii) from the first-acoustic-path first transducer;

and wherein the second acoustic receiver means comprises:
a second-acoustic-path first transducer for receiving the second acoustic signal during a third time separate from the first and the second times and, further, for projecting at a fourth time separate from any of the first time and the second time and the third time, a fourth acoustic signal (i) diagonally across the flowing fluid (ii) along the second acoustic path (iii) in the second direction;

and wherein the second acoustic transmitter means comprises:
a second-acoustic-path second transducer for projecting the second acoustic signal during the third time and, further, for acoustically receiving during the fourth time the fourth acoustic signal (i) diagonally across the flowing fluid (ii) along the second acoustic path from the second-acoustic-path first transducer.

5. The acoustic transit-time flowmeter according to claim 4 further comprising:
bi-directional electrical connection means for bi-directionally electrically connecting the first-acoustic-path first transducer to the second-acoustic-path second transducer so that an electrical signal produced by the first-acoustic-path first transducer in response to the receipt of the third acoustic signal is electrically communicated to the second-acoustic path second transducer, so that an electrical signal produced by the second-acoustic-path second transducer in response to receipt of the fourth acoustic signal is electrically communicated to the first-acoustic-path first transducer, and so that acoustic communication on the first acoustic path and on the second, acoustic path is at different times in either direction, but is always in the same direction on one acoustic path as it is on the other acoustic path.

6. The acoustic transit-time flowmeter according to claim 5 wherein the bi-directional electrical connection means comprises:
a bi-directional amplifier means for imparting gain to the electrical signals produced by each of the first-acoustic-path first transducer and the second-acoustic-path second transducer.

7. An acoustic transit-time flowmeter repetitively propagating acoustic signals, the flowmeter comprising:
a first acoustic transducer pair, located on opposite sides of a conduit flowing a fluid,
for bi-directionally transmitting a first acoustic signal at first times in a first direction relative to the fluid flow, and at second times in an opposite, second, direction relative to the fluid flow, (i) obliquely across the flowing fluid (ii) along a first acoustic path; and
for bi-directionally receiving the first acoustic signal at the first times from the second direction, and at the second times from the first direction, (i) obliquely across the flowing fluid (ii) along the first acoustic path;

a second acoustic transducer pair, located on opposite sides of a conduit flowing a fluid,
for bi-directionally transmitting a second acoustic signal at the first times in the first direction, and at the second times in the second direction, (i) obliquely across the flowing fluid (ii) along a second acoustic path; and for bi-directionally receiving the second acoustic signal at the first times from the second direction, and at the second times from the first direction, (i) obliquely across the flowing fluid (ii) along the second acoustic path; electrical connection means for electrically connecting the first pair to the second transducer pair so that the first acoustic signal transmitted and received by the first transducer pair is re-transmitted and re-received by the second transducer pair as the second acoustic signal;

wherein acoustic signal propagation is at the first times in the first direction along both the first acoustic path and the second acoustic path, and is at the second times in the second direction along both the first acoustic path and the second acoustic path.

8. The acoustic signal propagating transit-time flowmeter according to claim 7 wherein a one of the second acoustic transducer pair operating, at any one time, as a transmitting transducer is displaced in position in the second direction from a one the first transducer pair that is operating as a receiving transducer;

wherein a one of the second acoustic transducer pair operating, at the same time, as a receiving transducer is displaced in position in the first direction from a one of the first transducer pair that is operating as a transmitting transducer;

wherein an acoustic path from the transmitting one of the first transducer pair to the receiving one of the first transducer pair is both (i) geometrically directionally opposite, and (ii) at least partially overlapping, of an acoustic path from the transmitting one of the second transducer pair to the receiving one of second transducer pair.

9. The repetitive acoustic signal propagating transit-time flowmeter according to claim 7 wherein the first acoustic transducers are positioned diagonally across the conduit from one another, the diagonal forming a first leg "/" of the letter "X"; and wherein the second acoustic transducers are positioned diagonally across the conduit from one another, the diagonal forming a second leg " \ " of the letter "X";

wherein the first acoustic path and the second acoustic path are not only geometrically directionally opposite, but are folded with at least one acoustic path partially overlapping the other.

* * * * *